(12) United States Patent
Romero Ormazabal et al.

(10) Patent No.: US 9,497,980 B2
(45) Date of Patent: Nov. 22, 2016

(54) REDUCTION OF NON-STARCH POLYSACCHARIDES AND ALPHA-GALACTOSIDES IN SOY FLOUR BY MEANS OF SOLID-STATE FERMENTATION USING CELLULOLYTIC BACTERIA ISOLATED FROM DIFFERENT ENVIRONMENTS

(71) Applicant: Universidad de Chile, Santiago (CL)

(72) Inventors: Jaime Moisés Romero Ormazabal, Santiago (CL); Rafael José Daniel Opazo Salas, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 14/376,214

(22) PCT Filed: Jan. 29, 2013

(86) PCT No.: PCT/IB2013/050763
§ 371 (c)(1),
(2) Date: Aug. 1, 2014

(87) PCT Pub. No.: WO2013/114282
PCT Pub. Date: Aug. 8, 2013

(65) Prior Publication Data
US 2015/0030637 A1    Jan. 29, 2015

(30) Foreign Application Priority Data

Feb. 3, 2012 (CL) .................................... 296-2012

(51) Int. Cl.
| | | |
|---|---|---|
| A23L 1/20 | (2006.01) |
| A23K 1/00 | (2006.01) |
| C12N 1/20 | (2006.01) |
| A61K 36/48 | (2006.01) |
| C12R 1/465 | (2006.01) |
| C12R 1/01 | (2006.01) |
| A61K 35/74 | (2015.01) |

(52) U.S. Cl.
CPC ............... *A23K 1/007* (2013.01); *A23K 10/12* (2016.05); *A23K 50/30* (2016.05); *A23K 50/40* (2016.05); *A23K 50/80* (2016.05); *A23L 11/00* (2016.08); *A23L 11/07* (2016.08); *A23L 11/09* (2016.08); *A61K 36/48* (2013.01); *C12N 1/20* (2013.01); *C12R 1/01* (2013.01); *C12R 1/465* (2013.01); *A61K 35/74* (2013.01); *A61K 2236/19* (2013.01)

(58) Field of Classification Search
CPC ....... A23L 11/09; A23L 11/00; A23K 10/12; C12R 1/00; A61K 2236/10
USPC ........... 424/282.1; 435/252.1, 253.1; 426/46, 426/630
See application file for complete search history.

(56) References Cited

FOREIGN PATENT DOCUMENTS

KR    WO 2011031020 A2 *  3/2011 ............. A23K 1/007

OTHER PUBLICATIONS

Anonymous. Animal-Free Peptones and Yeast Extracts; BD Bionutrients Technical Manual (2015), downloaded from https://www.bdbiosciences.com/documents/tat_animalfree_peptones.pdf on Nov. 24, 2015.*
Opazo et al. Reduction of Soybean Meal Non-Starch Polysaccharides and Alpha-Galactosides by Solid-State Fermentation Using Cellulolytic Bacteria Obtained From Different Environments; PLOS one, vol. 7, No. 9 (Sep. 2012) pp. 1-10.*

* cited by examiner

Primary Examiner — Scott Long
Assistant Examiner — Paul Martin
(74) Attorney, Agent, or Firm — Blank Rome LLP

(57) ABSTRACT

The invention relates to a method for fermenting soy flour in the solid state in order to reduce non-starch polysaccharides and alpha-galactosides, said method comprising the following steps: a) preparation of the fermentation substrate; b) inoculation of the substrate with selected celluloytic bacterial strains; c) incubation; and, optionally, d) drying of the product, which generates a product with: an increase in protein of between 12 and 15% compared to non-fermented soy flour, degradation of the alpha-galactosides of more than 90% compared to non-fermented soy flour, a reduction in non-starch polysaccharides (NSPs) of between 15 and 25%, an amino acid profile similar to that of non-fermented soy flour, and immune-stimulating effects.

15 Claims, 10 Drawing Sheets

Non inoculated    Inoculated

Non inoculated    Inoculated

REDUCTION OF NON-STARCH POLYSACCHARIDES AND ALPHA-GALACTOSIDES IN SOY FLOUR BY MEANS OF SOLID-STATE FERMENTATION USING CELLULOLYTIC BACTERIA ISOLATED FROM DIFFERENT ENVIRONMENTS

This application is the U.S. national phase of International Application No. PCT/IB2013/050763, filed Jan. 29, 2013, which claims the benefit of Chilean Patent Application No. 2012-00296, filed Feb. 3, 2012.

FIELD OF THE INVENTION

The invention relates to the feed industry, particularly the animal feed industry and more particularly with the fish feed industry, specially salmons. It also relates to solid-state fermentation processes using cellulolytic bacteria.

BACKGROUND OF THE INVENTION

The halt in the extraction of wild marine resources has put a stop to fish flour availability worldwide and has increased prices (>1400 USD/ton) (International Monetary Fund). As a consequence the diets used in the production of aquiculture species like salmons have partially substituted this important consumable by other proteic ingredients among which the proteic consumables of vegetable origin stand out. Among these consumables the soybean meal, a sub-product of soy oil production, provides important advantages due to its low cost (<400 USD/Ton), its adequate proteic contents approximately 48% and a balanced amino acids profile (International Monetary Fund). Anyhow, its inclusion within the diets for salmons does not exceed 25% (replacement for fish meal) because higher rates of this consumable produce morphologic alterations of the salmon bowel which in turn produce a reduction in the productive parameters of the fish/salmonids (growth). These adverse effects have been attributed to the presence of different anti-nutritional factors (ANFs) where the thermostable ANFs stand out.

The soybean meal ANFs include some carbohydrates, like alpha-galactosides and non-starch polysaccharides (NSPs) (Choct, M.; rsjant-Li Y.; McLeish, J.; Peisker, M. 2010, Soy Oligosaccharides and Soluble Non-starch Polysaccharides: A Review of Digestion, Nutritive and Anti-nutritive Effects in Pigs and Poultry. *Asian-Australasian Journal of Animal Sciences*, 23, 1386-1398; Francis, G.; Makkar, H.; Becker, K. 2001, Anti nutritional factors present in plant-derived alternate fish feed ingredients and their effects in fish, *Aquaculture*, 199, 197-227; Karr-Lilienthal, L. K.; Kadzere, C. T.; Grieshop, C. M.; Fahey, G. C. 2005, Chemical and nutritional properties of soybean carbohydrates as related to no ruminants: A review. *Livestock Production Science*, 97, 1-12). The main alpha-galactosides contained in the soybean meal are the stachyose and the raffinose and its concentrates ranges from 2 and 5% w/w and 0.5 and 2% w/w of dry product respectively. (Choct, M.; rsjant-Li Y.; McLeish, J.; Peisker, M. 2010, Soy Oligosaccharides and Soluble Non-starch Polysaccharides: A Review of Digestion, Nutritive and Anti-nutritive Effects in Pigs and Poultry. *Asian-Australasian Journal of Animal Sciences*, 23, 1386-1398; Karr-Lilienthal, L. K.; Kadzere, C. T.; Grieshop, C. M.; Fahey, G. C. 2005, Chemical and nutritional properties of soybean carbohydrates as related to no ruminants: A review. *Livestock Production Science*, 97, 1-12). The total concentration of NSPs in the soybean meal is of around 15-20% of dry weight. This term (NSPs) groups three different types of polysaccharides: cellulose, hemicelluloses and pectins (Huisman, M. M. H.; Schols, H. A.; Voragen, A. G. J. 1998, Cell wall polysaccharides from soybean (*Glycine max.*) meal. Isolation and characterization. *Carbohydrate Polymers*, 37, 87-95; Karr-Lilienlhal, L. K.; Kadzere, C. T.; Grieshop, C. M.; Fahey, G. C. 2005, Chemical and nutritional properties of soybean carbohydrates as related to no ruminants: A review. *Livestock Production Science*, 97, 1-12; Knudsen, K. E. B. 1997, Carbohydrate and lignin contents of plant materials used in animal feeding. *Animal Feed Science and Technology*, 67, 319-338).

The deleterious of the ANFs was documented both for the alpha-galactosides and the NSPs in different animal species. In pigs, the NSPs and alpha-galactosides supplement has shown an adverse effect in growth (Choct, M.; rsjant-Li Y.; McLeish, J.; Peisker, M. 2010, Soy Oligosaccharides and Soluble Non-starch Polysaccharides: A Review of Digestion, Nutritive and Anti-nutritive Effects in Pigs and Poultry, *Asian-Australasian Journal of Animal Sciences*, 23, 1386-1398; Karr-Lilienthal, L. K.: Kadzere, C. T.; Grieshop, C. M.; Fahey, G. C. 2005, Chemical and nutritional properties of soybean carbohydrates as related to no ruminants: A review. *Livestock Production Science*, 97, 1-12). In poultry, the NSPs alter the digestion of nutrients because the lack of digestive enzymes and the soluble part of the NSPs create a viscous condition in the small intestine, altering the activity of the digestive enzymes. The alpha-galactosides reduce the body weight, the average daily weight gain and the feed conversion ratio (Choct, M.; rsjant-Li Y.; McLeish, J.; Peisker, M. 2010, Soy Oligosaccharides and Soluble Non-starch Polysaccharides: A Review of Digestion, Nutritive and Anti-nutritive Effects in Pigs and Poultry. *Asian-Australasian Journal of Animal Sciences*, 23, 1386-1398; Karr-Lilienthal, L. K.; Kadzere, C. T.; Grieshop, C. M.; Fahey, G. C. 2005, Chemical and nutritional properties of soybean carbohydrates as related to no ruminants: A review. *Livestock Production Science*, 97, 1-12). In aquaculture species the NSPs and alpha-galactosides are also considered anti nutritional factors (Francis, G.; Makkar, H.; Becker, K. 2001, Anti nutritional factors present in plant-derived alternate fish feed ingredients and their effects in fish. *Aquaculture*, 199, 197-227). Their presence in the diet of salmons increase the contents of water and minerals in the feces and block up the action of digestive enzymes (Francis, G.; Makkar, H.; Becker, K. 2001, Anti nutritional factors present in plant-derived alternate fish feed ingredients and their effects in fish. *Aquaculture*, 199, 197-227).

In aquaculture the situation is critical because the aquaculture species such as salmon have higher protein requirements than poultry or pig (Wilson, R.; John, H.; Hardy, R 2002. Amino Acid and Proteins. in: H. John, R. Hardy (Eds.), Fish Nutrition. Academic Press, 3rd Edition, pp. 143.179) and at present the replacement of fish meal using other protein ingredients is a challenge for this industry (Gatlin, D.; Barrows, F.; Brown, P.; Dabrowski, K.; Gaylord, T.; Hardy, R; Herman, E.; Hu, G.; Krogdahl., A.; Nelson, R; Overturf, K.; Rust, M; Sealey, W.; Skonberg, D.; Souza, J.; Stone, D.; Wilson, R.; Wurtele, E. 2007, Expanding the utilization of sustainable plant products in aqua feeds: a review. *Aquaculture Research*, 38, 551-579; Tacon, A. G. J.; Metian, M. 2008, Global overview on the use of fish meal and fish oil in industrially compounded aqua feeds: Trends and future prospects. *Aquaculture*, 285, 146-158).

There are reduction alternatives by aqueous or alcoholic extraction of the ANFs which generate a product known as soy protein concentrate which increases its protein contents in approximately 65% as compared to the soybean meal. By including this product in fish diets the productive levels increase because it increases the digestion of nitrogen or amino acids, it increases the growth ratio and the feed conversion ratio. (Choct, M.; rsjant-Li, Y.; McLeish, J.; Peisker, M. 2010. Soy Oligosaccharides and Soluble Non-starch Polysaccharides: A Review of Digestion, Nutritive and Anti-nutritive Effects in Pigs and Poultry. *Asian-Australasian Journal of Animal Sciences*, 23, 1386.1398; Olli, J. J., Krogdahl, A.; Vandeningh, T. S. G. A.; Brattas, L. E. 1994, Nutritive-Value of 4 Soybean Products in Diets for Atlantic Salmon (Salmo-Salar, L). *Acta Agriculturae Scandinavica Section A-Animal Science*, 44, 50-60). Nevertheless the cost of these consumables is similar to the one of fish meal restricting its use by the salmon culture industry. (Gatlin, D.; Barrows, E; Brown, P.; Dabrowski, K.; Gaylord, T.; Hardy, R; Herman, E.; Hu, G.; Krogdahl, A.; Nelson, R.; Overturf, K.; Rust, M.; Sealey, W.; Skonberg, D.; Souza, J.; Stone, D.; Wilson, R.; Wurtele, E. 2007, Expanding the utilization of sustainable plant products in aqua feeds: a review. *Aquaculture Research*, 38, 551-579). Another technology is the incorporation of glucohydrolases in the animal feed, although the effects of this alternative in productive trials have not produced concluding results in poultry, pigs or salmons (Bhat, M. K. 2000, Cellulases and related enzymes in biotechnology. *Biotechnol. Adv.*, 18, 355-383; Caeter, C. G.; Houlihan, D. F.; Buchanan, B.; Michell, A. 1. 1994, Growth and feed utilization efficiencies of seawater Atlantic salmon, Salmo salar L, fed a diet containing supplementary enzymes. *Aquaculture Research*, 25, 37-46; Choct, M.; rsjant-Li, Y.; McLeish, J.; Peisker, M. 2010. Soy Oligosaccharides and Soluble Non-starch Polysaccharides: A Review of Digestion, Nutritive and Anti-nutritive Effects in Pigs and Poultry. *Asian-Australasian Journal of Animal Sciences*, 23, 1386-1398). The inclusion of cellulases, hemicellulases and pectinases in salmon feeds poses an important restriction regarding temperature. This is because the body temperature of the salmon corresponds to the aquatic environment in which they are, in Chile is 10-12° C. In contrast, the activity optimal temperature of these enzymes is 50° C. (Bhat, M. K, 2000, Cellulases and related enzymes in biotechnology. Biotechnol. Adv., 18, 355-383; Caeter, C. G.; Houlihan, D. F.; Buchanan, B.; Michell, A. I. 1994, Growth and feed utilization efficiencies of seawater Atlantic salmon, Salmo salar L., fed a diet containing supplementary enzymes. Aquaculture Research, 25, 37-46).

Biotechnological methods such as fermentation with bacteria, yeasts and fungi in solid state for the lignocellulosic biodegradation of agricultural sub-products such as soybean meal have also been proposed (Graminha, E. B. N.; Gongalves, A. Z. L.; Pirota, R. D. P. B.; Balsalobre, M. A. A.; Da Silva, R.; Gomes, E. 2008, Enzyme production by solid-state fermentation: Application to animal nutrition. *Animal Feed Science and Technology*, 144, 1-22).

The fermentation of soybean meal is a process that allows the decrease or the degradation of different anti-nutritional factors producing a consumable which use in animal production (like salmons, poultry and pigs) could offer important benefits over the soybean meal without fermenting. This situation would be especially attractive considering the possibility of degrading the thermostable ANFs. In this regards different microorganisms and types of fermentations have been proposed for the reduction of anti nutritional factors. For example fermentations with *Debaryomyces hansenii* or *Lactobacillus brevis* in which the degradation of alpha-galactosides (GOSs) has been assessed (Refstie, S. Sahlstrom; S., Brathen, E.; Baeverfjord, G.; Krogedal, P. 2005, Lactic acid fermentation eliminates indigestible carbohydrates and anti nutritional factors in soybean meal for Atlantic salmon (Salmo salar). *Aquaculture*, 246, 331-345; Rodrigues Brasil, A; Tabarez de Rezende, S.; do Carmo Gouveia, M.; Guimaraes, V. 2010, Removal of oligosaccharides in soybean flour and nutritional effects in rats, *Food Chemistry*, 118, 251-255). On the other hand fermentations with *Aspergillus oryzae* fungi or with *Bacillus subtillis* have been developed for the reduction of lectins or tripsin inhibitor (Hong, K.-J.; Lee, C.-H.; Kim, S. W. 2004, *Aspergillus oryzae* GB-107 Fermentation Improves Nutritional Quality of Food Soybeans and Feed Soybean Meals. *Journal of Medicinal Food*, 7(4), 430-435; Kim, S. W.; van Heugten, E.; Ji, F.; Lee, C. H.; Mateo, R. D. 2010, Fermented soybean meal as a vegetable protein source for nursery pigs: I. Effects on growth performance of nursery pigs. *Journal of Animal Science*, 88, 214-224; Wang, J. P.; Liu, N.; Song, M. Y.; Qin, C. L.; Ma, C. S. 2011, Effect of enzymolytic soybean meal on growth performance, nutrient digestibility and immune function of growing broilers. *Animal Feed Science and Technology*, 169 (3-4), 224-229).

There is a need for developing a process that may allow the obtention of a product suitable for feed, particularly for animals, more particularly for fish, especially for salmons that contains high contents of protein higher than 50% a balanced amino-acid profile and low contents of ANFs.

Soy bean fermentation for human feed purposes is a millenary procedure in Asian cultures like China, Japan, Thailand and India, among others. The fermentation can be made directly on ground soy or to its by-products like the soybean meal or soy milk and tofu, a curdle of soy milk. The fermentation of soy curdle (tofu) is produced by a fermentation in solid state with some strains of fungi like *Actinomuco* sp, *Mucorwutungkino* sp, *Mhimelis* sp, and *Thizopuz* sp. There are commercial strains that correspond to *Actinomuco*. The process is performed at a temperature between 25° C. and 30° C., anyhow in warm summers the strains of *Thizopus oligosporus* are more suitable because they grow at temperatures like 40° C. In China a soy *fermentum* with *Aspergillus* and *Mucor* strains or with bacterial strains is also produced and is known as douchi or touchi. In Japan this product is known as *natto* and there are three different products: *Otohiki-natto* which is made based on an inocculate of *Bacillus natto* which is a variant of *Bacillus subtilis*. In these cases the fermentation is done at a temperature between 40-45° C. On the other hand there is the *yuki-wari* which corresponds to a mixture of the former with rice, inoculated with *koji*. *Koji* means a "fungi lint" and it generally corresponds to the growth on an *Aspergillus oryzae* and *Aspergillus sojae* grain in a 20 days fermentation at 25° C.-35° C. Finally, the third product is known as the *hama-natto* which corresponds to a mixture of soy with rice, wheat and barley inoculated with *koji*, then an aging of one year in pressure is done.

The *fermentum* of soy pastes in Asia is known as *miso*. The process also contains a mixture of soy bean soaked in water and then boiled. This soy paste is mixed with *koji* and with other strains of fungi and bacteria like: *Zygosaccharamyces rouxii*, *Torulopsis*, *Pediococcus*, *Halophilus* and *Streptococcus faecalis*. This paste is known as green *miso* and corresponds to an anaerobic fermentation at temperatures of 25° C.-30° C., and it undergoes a period of aging that varies from one week in the case of "white *miso*" up to months or a year. This product is frequently used in the preparation of soups. Another very important Asian fermented product from soy is the soy sauce. There are at least 5 types of soy sauces recognized in Japan and two production processes are described that vary in the type of fermentation, one with an aerobic fermentation and another one with anaerobic fermentation. The most classic process is the aerobic which starts from the soybean meal without oil. This is soaked and dried, cooked at 130° C. during 45 minutes and mixed with roasted barley meal. This mixture is then inoculated with *koji*, brine is added and left to ferment for some days. Later there is an aging in controlled conditions of salt and temperature being the latter of 35° C.-40° C. during a 2 to 4 months period. This widely known processes are not related to the process or the product of this invention which uses a specific combination of four cellulolytic bacteria to perform a solid state fermentation of the soybean meal to decrease the anti-nutritional factors.

The document WO 2009065722 presents a method to ferment a substrate that contains a soy protein. The method comprises the steps of providing a sterile aqueous fluid containing 0.5 to 8% per weight of dissolved soy protein, 0 to 0.2% per weight of dairy protein and less than 24% per weight of solids; inoculating a fluid with a culture comprising bacteria from the group of selected lactic or acid lactic bacteria consisting of mesophilic *Lactococcus, Leuconostoc, Lactobacillus* (with optimal temperature under 35° C.) and combinations thereof; fermenting the inocculatid fluid by incubating at 20° C.-40° C. during 0.5 to 11 hours; wherein during the fermentation the following changes in the concentrations occur: the diacetil concentration increases in at least 0.2 ppm and/or the acetaldehyde concentration increases by at least 0.1 ppm; the concentration of at least an n-alcanal $C_5$-$C_9$ decreases at least by 30% and/or the concentration of trans-2-hexenal decreases in at least by 30%. The document is not related to the fermentation of soybean meal to the decrease of anti-nutritional factors using cellulolytic bacteria.

The document WO 2005032568 describes a soy product fermented by lactic acid fermentation that has a strong immunopotentiator effect and a favourable flavour and a process to produce it. The product is produced fermenting soy and a processed soy product through a co-culture of lactic acid bacteria with a yeast. The lactic acid bacteria is at least *Enterococcus faecalis*, optionally combined with another coccus, bacilli or bifidobacteria. The yeast is *Saccharomyces cerevisiae* and/or *Saccharomyces rosei*. The fermented soy is produced fermenting soy milk using the mentioned microorganisms, to provide a liquid fermented product that is then neutralized with a calcium compound and later dried to result in a powder fermented product. The document is not related to the fermentation of soybean meal to decrease anti-nutritional factors using cellulolytic bacterria.

The document WO 2002085131 presents a method to produce a tasty product from a protein source using a combination of two different strains of bacteria. The protein source can be soy, wheat or rice but it is preferable milk or whey. The first strain is selected among *Macrococcus, Micrococcus, Enterococcus, Staphylococcus, Brevibacterium, Anthrobacter* and *Corynebacterium*, preferably *Macrococcus caseolyticus*. The second strain is selected among *Lactococcus, Lactobacillus, Pediococcus* or *Leuconostoc*. The source of protein is fermented with the bacteria at a pH above the isoelectric point of the protein, preferably at a pH of 5.5 to 6.5. The document is not related to the fermentation of soybean meal to decrease anti-nutritional factors using cellulolytic bacteria.

The document CN102210412 describes a compound feed to improve the meet ratio of the *Tilapia mossambica* and a method to prepare it. The compound feed mainly contains fermented rapseed meal and fermented soybean meal and is effectively absorbed during the digestion. Both fermented meals are available in the market therefore detail of the fermentation process used are not included. The document informs that the fermentation process eliminates tannins, trypsin inhibitors, and other anti-nutritional factors. Said document does not disclose a way to do the fermentation since the fermented meals used are available in the market.

The above mentioned documents are the closest documents to the present invention, anyhow the previous state of the art does not consider favouring the nutritional value of soybean meal an issue to be solved by decreasing the anti-nutritional agents like non-starch polysaccharides and alpha-galactosides. For that reason the state of the art does not consider that, in order to obtain this improvement, a combination of the three types of bacteria this invention proposes can be used and to be used in a soybean meal solid state fermentation procedure.

In addition to the documents of the mentioned patents, in the state of the art some industrial fermentation processes for soybean meal are known. Hamlet Protein AS, Horsens, Denmark sells fermented soybean meal through a biotechnological process with a product presenting a reduction in the contents of oligosaccharides an increase in the concentration of proteins and the elimination of anti-nutritional factors. The process this company uses is not completely clear, although in their patent applications US20060233913, WO 2011147923 and US20110034394A1 processes for soy, other seeds and yeast proteins fermentation are described by means of yeasts or specific enzymes. The use of cellulolytic bacteria to prepare the products of this company is not mentioned.

Dongguan Yinhua Biotechnology Co. Ltd, Dongguan, China also sells fermented soybean meal. The process they use to treat the soybean meal is not also completely clear, although in their patent application CN101161810 they disclose they do fermentation of soy and other seeds using yeasts. They do not mention the use of cellulolytic bacteria to prepare the products of this company.

Unlike that disclosed in the state of the art, the process of the invention does not use industrial or market available enzymes. It uses selected bacteria that supply their enzymes during the growth on the soybean meal.

BRIEF DESCRIPTION OF THE INVENTION

A solid fermentation process of soybean meal using 4 selected native microorganisms (see FIG. 1) to reduce the presence of alpha-galactosides by over 90% and around 20% of non-starch polysaccharides (NSPs) which are the thermostable ANFs of larger soy volume was developed. At the same time the fermentation makes it possible to increase the proteic proportion by around 13.5%. This allows the projection of larger inclusion levels of fermented soybean meal projecting a costs reduction of the food compounds formula for aquaculture species. The soybean meal reduced in anti-nutritional factors through the fermentation in solid state using native cellulolytic bacteria provides a nutritional and functionally excellent feed compound and at low cost. An additional feature is that the bacteria added in the bioprocess provides components that stay in the consumable and can act as immunostimulants providing a functional character to the developed consumable.

DETAILED DESCRIPTION OF THE INVENTION

Figure 1:
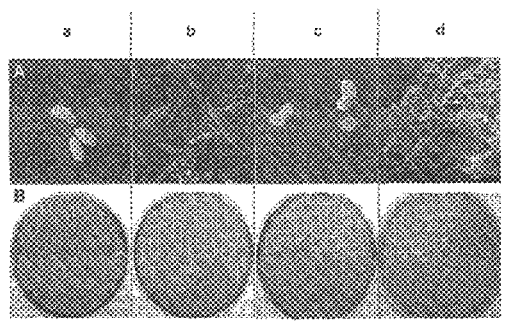
FIG. 1: Panel A shows pictures of the visualization of the strains selected in electronic microscope and panel B shows the cellulolytic activity measured with the Congo Red technique in the selected strains. A: CR18 *Streptomyces*; b: S7 *Cohnella*; c: T5 *Cellulosimicrobium*; d: L39 *Streptomyces*.
Figure 2A:
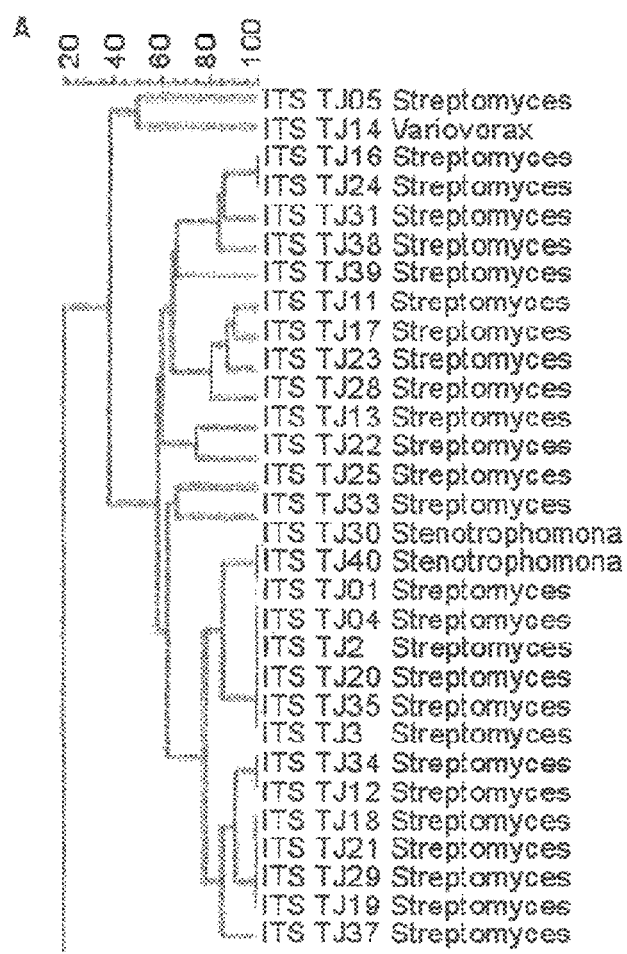
FIG. 2: Richness of the strains obtained by the 16S-23S rDNA intergenic spacer analysis. The genetic distance presented was measured by the DICE coefficient using the ITS profiles obtained. The dendograms were developed using the GelCompar II software with a 2% tolerance. A: Garden soil. B: Earthworm (*Eisenia foetida*). C: Corn silo. D. Termites (*Neotermes chilensis*). E: Decomposition leaves. F: Bovine rumen contents.
Figure 2B:
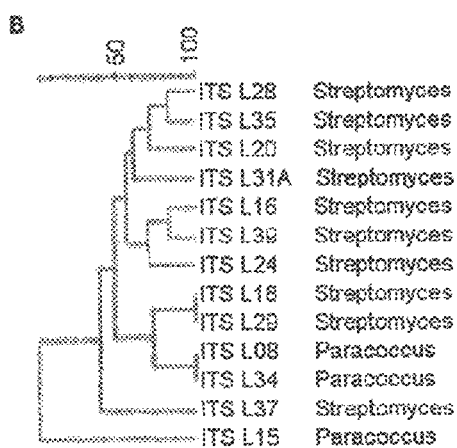
Figure 2C:
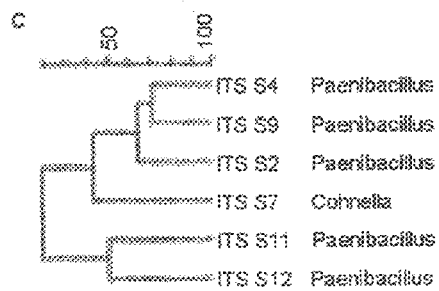
Figure 2D:
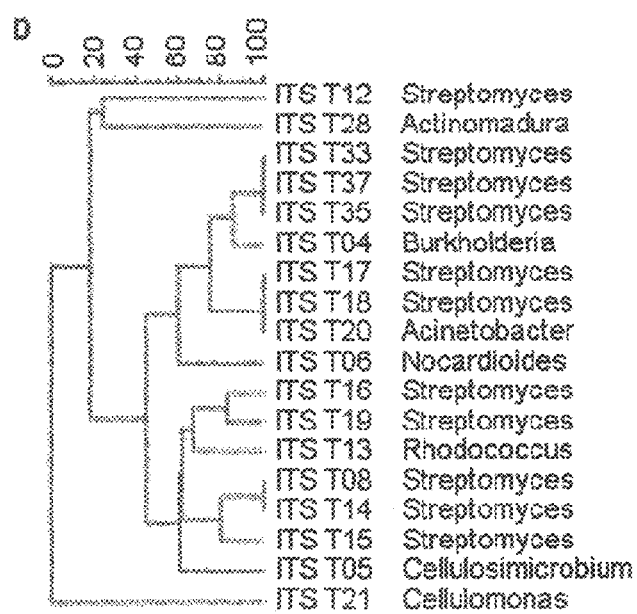
Figure 2E:
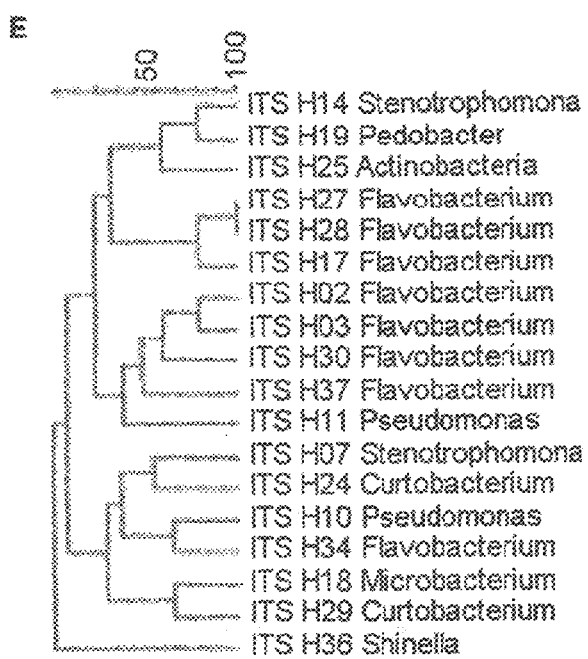
Figure 2F:
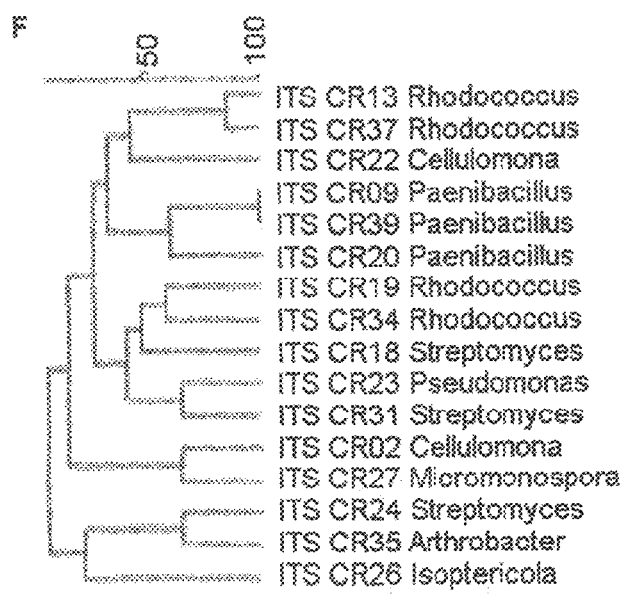
Figure 3A:
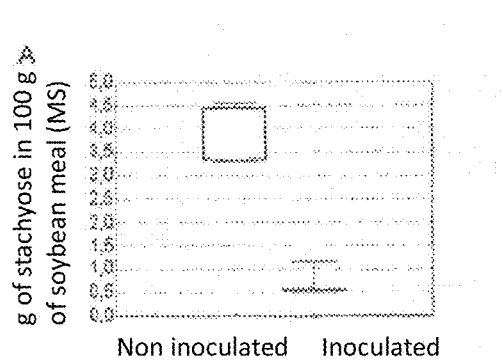
FIG. 3: Comparison between an inoculated group (with selected bacteria) and the non inoculated group in the contents of A: stachyose, B: raffinose, C: non-starch polysaccharides (NSPs) and D: protein.
Figure 3B:
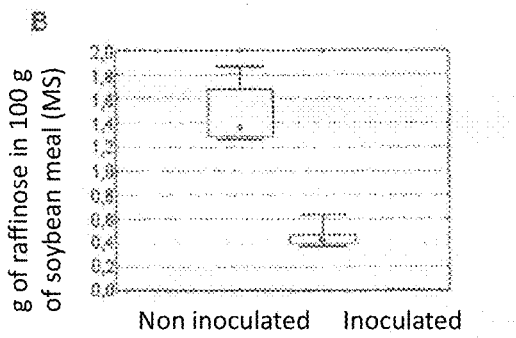
Figure 3C:
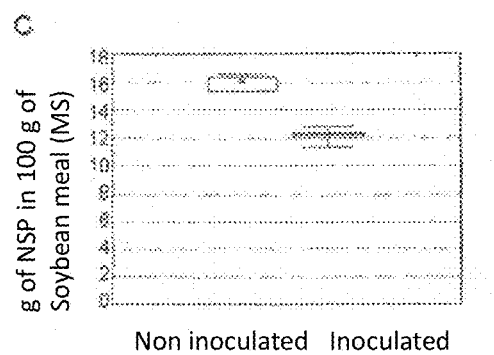
Figure 3D:
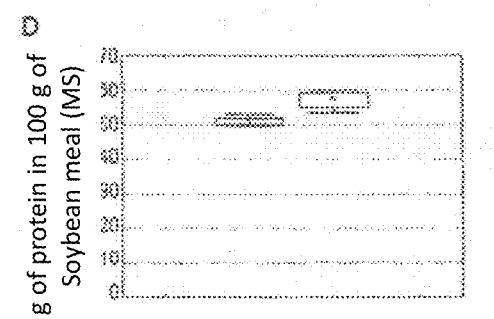

In order to decrease the anti-nutritional factors in the soybean meal, especially NSPs and alpha-galactosides, in order to increase its incorporation as consumable in the diet of animals, particularly fish, specially salmons, a solid fermentation process of soybean meal has been developed with the use of 4 selected native microorganisms that reduce over 90% the presence of alpha-galactosides and in around 20% the non-starch polysaccharides (NSPs) which are thermostable ANFs of higher volume in the soybean. At the same time the fermentation provides the increase of proteic proportion in around 13.5%.

The microorganisms for the fermentation process in solid state of soybean meal of this invention are selected based on the approach that in the natural environments, the degradation of complex polysaccharides happens thanks to the presence of a mixture of microorganisms. In the mixture every microorganism is aimed to its enzymatic specialty seeking to obtain simple sugars for its metabolism. The additional inclusion of a strain of fast growth in soy NSPs helps the consumption of products of the enzymatic reactions to prevent possible inhibitions per product. This is an important advantage when compared to processes based in a single microorganism.

To select the bacteria that take part in the solid state fermentation process of soybean meal, three key enzymatic activities were considered based on the structures of the glycosidic bonds of the NSPs and alpha-galactosides: cellulase, beta-xylanase and alpha-galactosidase. The NSPs present a more complex structure than the alpha-galactosides because they are a mixture of polymers: cellulose, hemicellulose and pectins. Moreover, the cellulose is an homogeneous polysaccharide comprised by sub-units of D-glucose linked by bonds beta(1-4)glycosidics which is degraded by the cellulases systems that specifically hydrolize these bonds (Perez, J.; Muñioz-Dorado, J.; de la Rubia, T.; Martinez, J. 2002, Biodegradation and biological treatments of cellulose, hemicellulose and lignin: an overview. *International Microbiology*, 5, 53-63). Because the cellulose corresponds to 30% w/w of the NSPs in the soybean meal (Knudsen, K. E. B. 1997, Carbohydrate and lignin contents of plant materials used in animal feeding. *Animal Feed Science and Technology*, 67, 319-338), this homopolymer was the first target considered to degrade NSPs using a solid state fermentation process.

In contrast the hemicellulose and pectins are heterogeneous polysaccharides that require various different hydrolase enzymes for the degradation. Therefore it is considered that the endo-1.4-beta-xylanase that hydrolizes the skeleton of the xylose present in the hemicellulose is a complementary activity useful in degrading the NSPs (Perez, J.; Muñioz-Dorado, J.; de la Rubia, T.; Martinez, J. 2002, Biodegradation and biological treatments of cellulose, hemicellulose and lignin: an overview. *International Microbiology*, 5, 53-63).

The alpha-galactosides are oligosaccharides consisting mainly of one or two units of bonded galactose 1,6-alpha, united by bonds 1,3-alpha to a saccharose terminal (Karr-Lilienthal, L. K.; Kadzere, C. T.; Grieshop, C. M.; Fahey, G. C. 2005, Chemical and nutritional properties of soybean carbohydrates as related to non ruminants: A review. *Livestock Production Science*, 97, 1-12). The hydrolysis of the saccharose disaccharide happens in the digestive tract of animals through the action of the enzyme saccharase. Therefore the reduction of the alpha-galactosides is focused on the hydrolysis of bonds 1.6-alpha-galactose by alpha-galactosidase.

Therefore a solid state fermentation process for soybean meal was designed in this invention where bacteria having cellulase, beta-xylanase and alpha-galactosidase activities are used in order to sequentially, controlled and rationally degrade anti-nutritional factors present in soybean meal that cause diseases and decrease of fish growth. The combination of the enzymatic activities of the selected bacteria together with a bacteria that presents a high growth in NSPs extracted from soy which helps consume the products and the enzymatic reactions to prevent possible inhibitions by product, provides a solid state fermentation process for soybean meal that produces a product with over 90% reduction of alpha-galactosides and approximately 20% reduction of NSPs since in the first place the most simple sugars are degraded and then the more complex ones and additionally through other enzymatic activities of the selected bacteria a pre-digestion of the proteins occur which generates a varied range of peptides containing a balanced profile of amino acids suitable for animal feeding, specially fish, particularly salmons.

For the rational selection of the bacteria for the process, samples were taken from environments where bacteria with the required activities are naturally found. Samples of garden soil, earthworms (*Eiseniafoetida*), com silo, termites (*Neotermes chilensis*) decomposition leaves and bovine rumen contents were taken. The samples were treated and cultured in order to isolate the different strains present in those environments. The phylogenetic identification of the strain was done amplifying the gen for the ribosomal RNA 16S rDNA, sequencing it and comparing it with the sequences present in the data base Ribosomal Data Project II (rdp.eme.mus.edu) to identify the bacterial gender.

Later the strains were analyzed for the three activities mentioned and the strains with better activities were chosen.

In the analysis for the cellulase activity two strains with high activity were selected belonging to the *Cohnella* sp and *Streptomyces* sp genders. In the analysis the beta-xylanase activity, a strain of the *Cellulosimicrobium* sp gender was selected because of its high activity. It was found that the strains previously selected for their cellulase activity also show alpha-galactosidase activity. Additionally a strain of the *Streptomyces* sp gender was selected that showed a fast growth on soy NSPs which help consume the products from the enzymatic reactions to prevent possible inhibitions by product.

Consequently, for the process of this invention four bacterial strains were selected from the *Streptomyces* sp, *Cohnella* sp and *Cellulosimicrobium* sp genders (FIG. 1).

The selected strains have been deposited under terms of the Budapest Treaty with the U.S. Agricultural Research Service Culture Collection (USDA, ARS, 1815 North University Street, Peoria, Ill., 61064) on Nov. 25 2011 under the following access numbers: NRRL B-50604 strain of the gender *Cohnella* sp, NRRL B-50603 strain of the gender *Cellulosimicrobium* sp, NRRL B-50602 strains of the gender *Streptomyces* sp, and NRRL B-50601 strains of the gender *Streptomyces* sp.

The strain NRRL B-50604 of the gender *Cohnella* sp is Gram positive, fusiform and has high total cellulolytic activity and high alpha-galactosidase activity. The strain NRRL B-50602 of the *Streptomyces* sp genderis Gram positive, has cocobacilli shape and high total cellulolitic activity and high alpha-galactosidase activity. The strain NRRL B-50603 *Cellulosimicrobium* sp of the gender is Gram positive, has coco shape and high endo-1.4-beta-xylanase activity. The strain NRRL B-50601 of the *Streptomyces* sp genderis Gram positive, has mycelium shape and shows a fast growth on NSPs extracted from soy.

The strains studied and selected are native and there molecular features make them traceable and distinguishable from other collection strains which assures its novelty especially when used combined with the four strains for the soybean meal fermentation process to decrease anti-nutritional factors.

Solid state fermentation process developed:

The solid state fermentation process of this invention comprises the steps of: a) preparation of the fermentation substrate; b) inoculating the substrate with the selected bacterial strains; and c) incubation. In a particular realization the process additional comprises the step of d) drying of the product.

The soybean meal required for this process must have ideally a particle size between 200 and 600 μm. In a particular realization the particle size of the soybean meal is of 400 μm.

Step a) the preparation of the fermentation substrate consists of mixing the soybean meal with water and then with the fermentation solution.

The step of the substrate preparation starts with the conditioning of the soybean meal in a container or closed chamber where water and a fermentation solution is added which comprises different minerals and salts that help the fermentation process. In a particular realization the fermentation solution to prepare 10 kilos of soybean meal/water with 7 liters water contains: 5 g $MgSO_4$, 1.22 g $CaCl$, 13.6 g $NH_4Cl$, 2.233 g $KCl$, 10 mg pentahydrate $FeSO_4$, 10 mg tetrahydrate $MnCl$, 10 mg pentahydrate $ZnSO_4$, 1.2 ml $H_3PO_4$ and 21.13 g $Na_2HPO_4$. The water is added in a proportion of water/soybean meal between 2:1 and 3:1 (v/w). In a particular realization the ratio of water weight to soybean meal is 2.4:1 (v/w).

Once the soybean meal is moistened the process goes to step b) inoculating the substrate with selected bacterial strains: strain NRRL B-50604 of the r *Cohnella* sp gende; strain NRRL B-50603 of the r *Cellulosimicrobium* sp gende; strains NRRL B-50602 and NRRL B-50601 of the *Strepto-* *myces* sp gender (see FIG. 1). In the inoculation step the substrate with the selected bacterial strains $1\times10^7$ and $1\times10^{11}$ cells per gram of substrate of each selected strain are inoculated. In a particular realization $1\times10^9$ cells per gram of substrate of each selected strain are inoculated.

Then comes step c) incubation. In this step the mixture of soybean meal, water, fermentation solution and bacteria is incubated for a period of time at an established temperature. The incubation step is done at 37° C. during 6 to 14 days with rotation movements (between 3 and 7 rpm, preferably 5 rpm). In a particular realization the incubation is done during 10 days. The purpose of the incubation is to regulate the pH of the process by adding a buffer with fermentation solution. This buffer has a pH of between 6.5 and 7.5. In a particular realization the buffer's pH is 7.0.

Once the incubation is finished, the fermented soybean meal can be sold at different moisture levels, although for its best conservation it might be necessary to decrease the contents of water through an optional drying process. Step d) drying of the product can be done with any known technique, as an example by spray drying, sublimation drying, vacuum heater or others or a combination thereof.

Advantages of the Process and the Generated Product

The former process does not use industrial or market available enzymes, it only uses microorganisms that supply their enzymes during the growth on soybean meal. This represents an important advantage in that it reduces costs.

With the former process a product with a protein increase of around 13.5 (between 12 and 15%), degrading of almost all the alpha-galactosides (higher than 90%) and around 20% reduction of NSPs (between 15 and 25%) is obtained. Moreover, the process does not affect the amino acids profile of the soybean meal (see FIG. 5), showing even after the fermentation a balanced and suitable profile for animals' nutrition, specially fish, particularly salmons. Additionally, the process has a comparative advantage which is that the selected bacteria do not produce toxic compounds like the biogenic and toxic amines, as it happens in processes that use fungi.

Another important feature of the process is that it is done with a very low water to substrate weight ratio between 2:1 and 3:1 (v/w), which decreases the subsequent drying costs.

The characteristics of the new product, the fermented soybean meal with decreased anti-nutritional factors allows considering higher levels of fermented soybean meal inclusion projecting a reduction in costs of the formulation of feed for aquaculture species. An additional feature is that the added bacteria in the fermentation bioprocess provide components that stay in the consumable and that may act as immunostimulant providing a functional feature to the developed consumable.

INDUSTRIAL APPLICATION

The specific field of application of this invention is the feed industry, particularly the feed industry for animals and more particularly the feed industry for fish, especially salmons. The soybean meal fermented with the process of the invention can be applied for the improvement of proteic consumables of vegetable origin, specifically of soybean meal. These consumables are used with restrictions for the formulas of animals' diets, specially in aquaculture diets. Its improvement through the process of the invention produces a consumable enriched in proteins and free of the anti-nutritional factors associated to oligosaccharides.

The projection of the consumable improved by the fermentation can be applied not only in the aquaculture field but also in the production of pigs, poultry and also in the field of pets.

It will be apparent for anyone skilled in the field that numerous variations and/or modifications can be done to the invention as has been described without moving apart from the scope of protection. The realizations described as well as the following examples are only for illustrative purposes and do not limit the invention.

APPLICATION EXAMPLES

Example 1

Isolation of Bacteria

The first step of this development was the isolation of bacteria from different environments and their further molecular characterization.

The following environments were chosen: garden soil, earthworms (*Eisenia foetida*), corn silo, termites (*Neotermes chilensis*), decomposition leaves and bovine rumen contents.

The samples taken from those environments were immediately processed after their collection. The samples were crushed, weighed and homogenized in sterile PBS buffer. Then they were seeded in minimum solid medium of carboximetilcellulose containing: carboximetilcellulose 5 g (Merck), $NH_4Cl$ 6 g, $Na_2HPO_4$ 0.6 g, BactoAgar 15 g, Amphotericin B 10 mg and traces of essential elements of Hendriks (Hendricks, C. W.; Doyle, J. D. Hugley, B. 1995, A New Solid Medium for Enumerating Cellulose-Utilizing Bacteria in Soil, *Applied and Environmental Microbiology*, 61, 2016-2019) and 1 L water. The incubation was done for 5 days at 25° C. A total 240 bacteria colonies were selected that grew in the selected medium at different dilutions. From these 240 colonies, 113 bacterial strains showed cellulolytic activity measured by Congo Red (Ruijssenaars, H. J.; Hartmans, S. 2001, Plate screening methods for the detection of polysaccharase-producing microorganisms. *Applied Microbiology and Biotechnology*, 55, 143-149). FIG. 1 shows the analysis for the selected strains.

The phytogenetic identification of the cellulolytic strains was done by amplifying their 16S rDNA sequence. The genomic DNA was isolated from the bacterial cultures with the genomic DNA purification kit from Promega. The 16s amplifying corresponds from the position 341 to 907 (*E. coli* listing) and then for a better identification of the selected cellulolytic strains the 16S rDNA was almost completely amplified from the position 27 to 1492 (*E. coli* listing). The PCR reaction was made in a reaction mixture of 30 µL containing 0.2 mM of each dNTP (Invitrogen), 0.05 $UmL^{-1}$ of Taq DNA polymerase recombinant (Invitrogen), polymerase reaction buffer, 2 mM $MgCl_2$ and 0.25 µM $mL^{-1}$ of each initiator and 1.0 µL of genomic DNA of the strain. The initiators were 341, SEQ ID NO 1: CCT ACG GGA GGC AGC AG and 907, SEQ ID NO 2: CCG TCA ATT CMT TTG AGT TT for short sequence or 27F, SEQ ID NO 3: AGAGGTTTGATCCTGGCTCAG and 1492R, SEQ ID NO 4: GGTT ACCTTGTT ACGACTT for long sequence. The program of the thermo cycler was: initial pre-denaturation, 3 minutes at 95° C., then 30 cycles of denaturation during one minute at 95° C., aligning of initiators during 1 minute at 58° C., extension during one minute at 72° C. and final extension cycle during 7 minutes at 72° C. The sequencing was 'previously edited and was compared with the Ribosomal Data Project (rdp.eme.mus.edu) database to identify the bacterial gender.

In order to distinguish the level of the strain in the identified gender an amplification by PCR of the intergenic spacer (ITS) between the genes 16-13S rDNA was done. The PCR reaction was made with the same protocol described before but the initiators were L1, SEQ ID NO 5: GAA GTC GTA ACA AGG and G1, SEQ ID NO 6: CAA GGC ATC CAC CGT. The conditions for the PCR were as follows: initial pre-denaturation, 3 minutes at 95° C., then 30 cycles of denaturation during 30 minutes at 95° C., aligning of initiators during 1 minute at 58° C., extension during 1 minute at 72° C. and final cycle of extension during 7 minutes at 72° C. The PCR products were visualized in polyacrylamide gel electrophoresis and died with silver (Gonzalez, N.; Romero, J.; Espejo, R. T. 2003, Comprehensive detection of bacterial populations by PCR amplification of the 16S-23S rRNA spacer region, *Journal of Microbiological Methods*, 55, 91-97). The ITS 16S-23S rDNA profiles (ribosomal intergenic region between genes 16S and 23S, correspond to an internal transcribed spacer (ITS)) were analyzed with the Gel compare software (Applied Maths) with a position tolerance of 2%. The genetic distance was assessed based on the DICE coefficient using fragments of DNA.

With these analysis the identification of the isolated strain and their differentiation at strain level was established, see FIG. 2.

Representatives of each one of the ITS clusters obtained to make a selection with 3 enzymatic activities were then selected: total cellulolytic activity (EC 3.2.1.4; EC 3.2.1.9 1; 3.2.1.21), activity endo-1.4-beta-xylanase (EC 3.2.1.8) activity and 1.6-alpha-galactosidase (EC 3.2.1-22) activity. The latter was only assessed in a group of pre-selected strains with previous enzymatic activities.

The total cellulolytic activity and the endo-1.4-beta-xylanase activity were analyzed in an exploration trial assessing the isolated bacterial. Selected strains were subsequently assessed in a comparative trial making 8 copies for each strain. The total cellulolytic activity and the endo-1.4-beta-xylanase activity were analyzed with a supernatant of a bacterial culture in a minimum medium with soybean meal extract. This extract is obtained with the extraction process of NSPs proposed by Englyst et al. (Englyst, H. N.; Quigley, M. E.; Hudson, G. J. 1994, Determination of Dietary Fiber As Non starch Polysaccharides with Gas-Liquid-Chromatographic, High-Performance Liquid-Chromatographic or Spectrophotometric Measurement of Constituent Sugars. *Analyst*, 119, 1497-1509). Within the method this extract is specifically obtained after rinsing with acetone. This soybean meal extract is free of monosaccharides, olisaccharides and starch (Englyst, H. N.; Quigley, M. E.; Hudson, G. J. 1994, Determination of Dietary Fiber As Non starch Polysaccharides with Gas-Liquid-Chromatographic, High-Performance Liquid-Chromatographic or Spectrophotometric Measurement of Constituent Sugars. *Analyst*, 119, 1497-1509) and the contents of NSPs is of 30 mg in 100 mg of extract.

The enzymatic culture medium contained: soybean meal Englyst extract 20 mg, $NH_4Cl$ 12 mg, $Na_2HPO_4$ 1 mg in 2 ml water. $1 \times 10^7$ cells of each cellulolytic strain were inoculated in 2 ml of the former medium and were incubated during 4 days at 25° C. The total cellulolytic activity was evaluated through the method of filter paper with modifications with an incubation period of 24 hours at 50° C. (Ghose, T. 1987, Measurement of cellulase activities. *Pure & applied Chemistry*, 59, 257-268). The total cellulolytic activity unit was defined as the amount of µmols of glucose set free per minute per one ml of supernatant of bacterial culture (Nitisinprasert, S.; Temmes, A. 1991, The Characteristics of A New Non-Spore-Forming Cellulolytic Mesophilic Anaerobe Strain Cm126 Isolated from Municipal Sewage-Sludge. *Journal of Applied Bacteriology*, 71, 154-161). The endo-1.4-beta-xylanase activity was assessed through the method of p-nitrophenyl derivatives: p-nitrophenyl-beta-D-xylopyranoside. One unit of beta-xylanase activity was defined as the amount of μmols of p-nitrophenol set free per minute per one ml of supernatant of bacterial culture at 25° C. (Tirado, O.; Rosado, W.; Govind, N. S. 2005, Characterization of bacteria with carbohydrase activities from tropical ecosystems. *Journal of the Marine Biological Association of the United Kingdom*, 85, 269-275). The key for the selection of strains was the presence of significant and high enzymatic activities.

The alpha-D-galactosidase activity was assessed by the method of p-nitrophenyl derivatives: p-nitrophenyl-alpha-D-galactopyranoside galactopyranoside (Tirado, O.; Rosado, W.; Govind, N. S. 2005, Characterization of bacteria with carbohydrase activities from tropical ecosystems. *Journal of the Marine Biological Association of the United Kingdom*, 85, 269-275). A minimum medium containing: raffinose pentahydrate (Sigma, St. Louis, Mo., USA) 20 g, $NH_4Cl$ 6 g, $Na_2HPO_4$, 0.6 g and Bacto Yeast Extract 2.5 g in 1 L water was used in the trial. The apha-D-galactosidase activity unit was defined as the amount of enzyme set free by 1 μmol of p-nitrophenol per minute per ml of bacterial culture supernatant at 25° C. (Tirado, O.; Rosado, W.; Govind, N. S. 2005, Characterization of bacteria with carbohydrase activities from tropical ecosystems. *Journal of the Marine Biological Association of the United Kingdom*, 85, 269-275).

4 bacterial strains were selected based on their noted enzymatic activities, corresponding to the strains *Streptomyces* sp (NRRL B-50602 and NRRL B-50601), *Cohnella* sp (NRRL B-50604) and *Cellulosimicrobium* sp (NRRL B-50603).

Example 2

Fermentations in Solid State at Laboratory Scale

With the selected bacteria fermentation in solid state experiments were developed at laboratory scale to assess the degradation of the ANFs proposed, plus some factorial designs to optimize initially the process. The conditions found were validated with an experiment at laboratory scale with 5 copies where the contents of alpha-galactosides and NSPs were compared in two groups: one group with inoculum of selected bacteria ($1 \times 10^9$ cells per gram of substrate per each selected strain) and another group without inoculum in similar conditions and parameters.

The ferments conditions were as follows: in glass bottles with filtered aeration 30 g of soybean meal were added (with particle size of 400 μm and sterilized by gamma radiation with 25 kilo gray) and fermentation solution at a ratio of water to substrate of 2.4:1 (v/w) with a relative humidity near 85%. This was considered the substrate. The culture solution contained phosphate buffer 100 mM pH 7.0 with $MgSO_4.7H_2O$ 150 μg, $CaCl_2$ 36.5 μg, $NH_4Cl$ 408 μg, KCl 67 μg, $FeSO_4.7H_2O$ 30 μg, $MnCl_2.4H_2O$ 30 μg, and $ZnSO_4.7H_2O$ 30 μg for 30 g of substrate. The bottles were incubated with rotation movements (5 rpm) during 10 days at 37° C.

The NSPs were quantified by spectrophotometric measurement (Englyst, H. N.; Quigley, M. E.; Hudson, G. J. 1994, Determination of Dietary Fiber As Non starch Polysaccharides with Gas-Liquid-Chromatographic, High-Performance Liquid-Chromatographic or Spectrophotometric Measurement of Constituent Sugars. *Analyst*, 119, 1497-1509), the raffinose and the stachyose were extracted according to the method of Giannoccaro et al. (Giannoccaro, E.; Wang, Y. J.; Chen, P. Y. 2006; Effects of solvent, temperature, time, solvent-to-sample ratio, sample size, and defatting on the extraction of soluble sugars in soybean. *Journal of Food Science*, 71, C59-C64) and quantified by HPLC coupled to an Erma ERC-7510 Refractive Index Detector using a REZEX RSO oligosaccharides column (200 mm-10 mm: Phenomenex, Torrance, Calif., USA) kept at 60° C. HPLC grade water was used as eluent with a flow rate of 0.2 ml $mM^{-1}$ (LeBlanc, J. G.; Garro, M. S.; de Giori, G. S. 2004; Effect of pH on *Lactobacillus fermentum* growth, raffinose removal, alpha-galactosidase activity and fermentation products. *Applied Microbiology and Biotechnology* 65, 119-123) and the protein was quantified by with the Kjeldahl method (AOAC, 1990, Official Methods of Analysis of Association of Official Analytical Chemistry 15th Edition. Arlington Va., Method 960.52).

The results of the analysis of the ANFs are shown in FIG. 3 (A, B, C and D). The fermentation process in solid state with the selected bacteria showed that a reduction by 87.5% for the stachyose and 69% for the raffinose is produced. These sugars are the main alphagalactosides of the soybean meal. The NSPs were reduced by 24%. The process also supplied an 11.76% increase of the total contents of protein in the soybean meal with inoculate (FIG. 3D).

Example 3

Fermentations in Solid State at Larger Scale

Once obtained the objective at laboratory scale level, a fermentation chamber at larger scale was developed using the parameters previously established.

The fermentation solution was prepared according to Table 1.

TABLE 1

Fermentation solution for 10 kilos of soybean meal/water with 7 liters of water

| Compound | Qty for 10 kilos soybean meal/water, with 7 liters of water |
| --- | --- |
| $MgSO_4$ | 5 g |
| CaCl | 1.22 g |
| $NH_4Cl$ | 13.6 g |
| KCl | 2.233 g |
| Pentahydrated $FeSO_4$ | 10 mg |
| Tetrahydrated MnCl | 10 mg |
| Pentahydrated $ZnSO_4$ | 10 mg |
| $H_3PO_4$ | 1.2 ml |
| $Na_2HPO_4$ | 21.13 g |

The results for the reduction of the nutritional factors of this fermentation are shown in Table 2 and Table 3.

TABLE 2

Proximal chemical analysis of the soybean meal without fermentation and of the fermented soybean meal

| | Unit | Non-fermented Soybean meal | Fermented Soybean meal |
| --- | --- | --- | --- |
| Total protein | % | 46.83 ± 0.13 | 54.23 ± 0.14 |
| Ethereal extract | % | 7.77 ± 0.06 | 7.29 ± 0.06 |
| Non-nitrogenated extract | % | 26.56 ± 0.04 | 18.68 ± 0.26 |
| Energy | Kcal/100 g | 363.67 ± 0.58 | 357.00 ± 0.00 |

TABLE 3

Reduction of anti-nutritional factors in the fermentation
of soybean meal compared with non fermented soybean meal.

| | Unit | Non-fermented Soybean meal | Fermented Soybean meal |
|---|---|---|---|
| Stachyose | % | 4.23 ± 0.93 | ≤0.15 |
| Raffinose | % | 1.38 ± 0.15 | ≤0.15 |
| NSPs | % | 16.10 ± 0.17 | 13.89 ± 0.73 |

Figure 4:
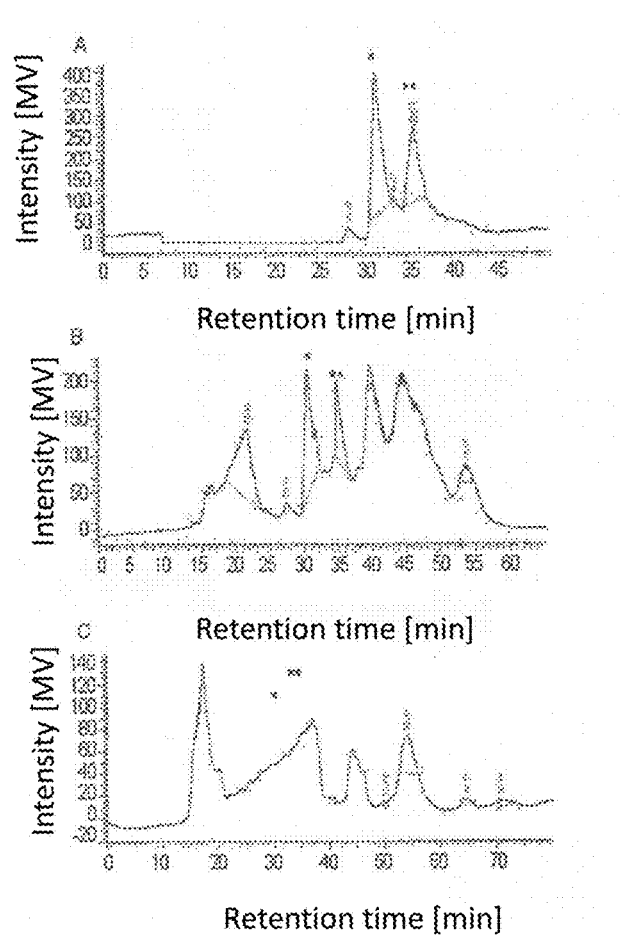
FIG. 4: A. Chromatogram of the stachyose and raffinose standards, B: chromatogram of the soybean meal without fermentation and C: chromatogram of the fermented soybean meal. *stachyose; **raffinose.

The results of the scaling process show that there is an increase in the contents of protein by approximately 15.8%. A reduction of the alpha-galactosides at non detectable levels for the HPLC technique was also observed suggesting a reduction of over 90% of them. FIG. 4 shows a chromatogram of A: the stachyose and raffinose standards, B: non-fermented soybean meal and C: fermented soybean meal obtained from the HPLC analysis. The reduction of NSPs was of 13.73%.

Figure 5:
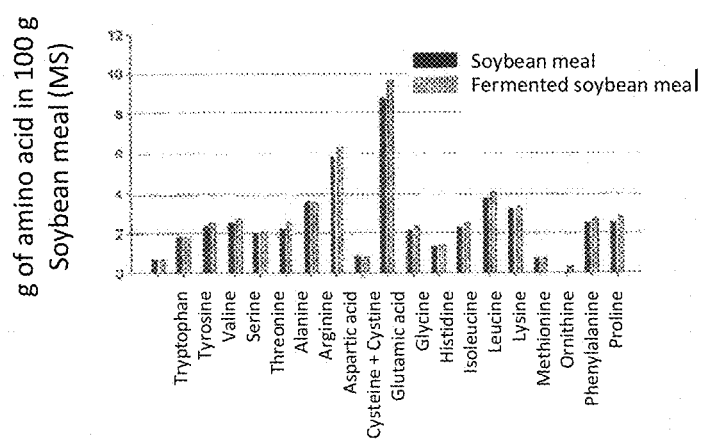
FIG. 5: Bar graph of the comparison in the amount of 19 amino acids (g in 100 g of soybean meal (MS)) between soybean meal and fermented soybean meal.

An analysis of the amino acids profile between the fermented and the non-fermented soybean meal was also done. The results are shown in FIG. 5. In general the amino acids profile does not show important variations keeping the normal balance of amino acids of the soy including its limitations in methionine and lysine.

Example 4

Functional Trials

Figure 6:
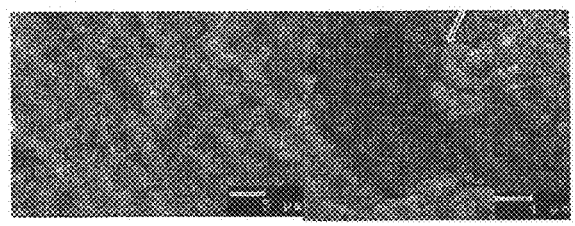
FIG. 6: Electronic microscope scanning showing the selected bacteria during the fermentation.

The bacterial strains used for the fermentation of soybean meal of this invention were assessed in its stimulation of the innate immune system of fish using the axenic zebrafish model (free of germs). In this model, larvae of 3 days post fertilization (dpf) were exposed to the bacteria until day 6 dpf when they were analyzed for their genic expression with quantitative PCR. Among the selected strains in the process two of the *Streptomyces* gender can be found, they both induce the expression of the C3 gene which belongs to the system of the complement which is one of the important responses of the innate immunity in fish. This protein favors the opsonization of microbes and their subsequent phagocytosis. This indicates that molecules derived from the bacteria included in the process (FIG. 6) and that are included in the final consumable, exert an immunostimulant effect in fish.

Example 5

Conclusions and Projections

The fermentation process in solid state with the selected cellulolytic bacteria allows reducing some of the thermostable ANFs of soy such like the alpha-galactosides (stachyose and raffinose) and NSPs. It also increases the contents of proteins by 13.5% approximately, keeping the amino acids profile. This protein increase impacts the process of diets formulation. Given that in the fermented soybean meal their is a larger proportion of proteins, this consumable delivers the protein levels considered in a diet using a lower volume of the consumable. As a consequence all the anti-nutritional factors of soybean meal decrease in its presence in the final feed. This benefits adds to the degradation of the GOSs and NSPs produced by the fermentation. The functional feature supplied when including the bacterial molecules in the consumable (FIG. 6) and proved in zebrafish, allows the projection of the consumable beyond a simple replacement of the soybean meal because it is also presented as an immunostimulant functional consumable.

Example 6

Properties of the Soybean Meal Free of
Alpha-Galactosides Oligosaccharides and Reduced
in Non-Starch Polysaccharides Obtained with the
Method of the Invention Table 4 shows the characteristics of soybean meal free of alpha-galactosides oligosaccharides and reduced in non-starch polysaccharides obtained with the method of the invention.

TABLE 4

Physical, chemical properties and anti-nutritional factors
contents in the soybean meal free of oligosaccharides
alpha-galactosides and reduced in non-starch polysaccharides
obtained with the method of the invention.

| | Unit | Non-fermented Soybean meal | Fermented Soybean meal |
|---|---|---|---|
| Physical properties | | | |
| Moisture | % | 8.4 ± 0.08 | 8.04 ± 0.06 |
| Chemical properties | | | |
| Total protein | % | 46.83 ± 0.13 | 54.23 ± 0.14 |
| Ethereal extract | % | 7.77 ± 0.06 | 7.29 ± 0.06 |
| Non-nitrogenated extract | % | 26.56 ± 0.04 | 18.68 ± 0.26 |
| Energy | Kcal/100 g | 363.67 ± 0.58 | 357.00 ± 0.00 |
| Anti-nutritional factors proposed | | | |
| Stachyose | % | 4.23 ± 0.93 | ≤0.15 |
| Raffinose | % | 1.38 ± 0.15 | ≤0.15 |
| NSPs | % | 16.10 ± 0.17 | 13.89 ± 0.73 |

The invention claimed is:

1. A solid state soybean meal fermentation method to reduce non-starch polysaccharides and alpha-galactosides, comprising the steps of a) preparation of a soybean meal fermentation substrate;

b) inoculating the substrate with a mixture of bacterial strains, wherein the mixture comprises:

i) a bacterial strain belonging to the *Cohnella* sp gender deposited on Nov. 25 2011 in the Agricultural Research Service Culture Collection (NRRL) of the U.S. Department of Agriculture with access number NRRL B-50604;

(ii) a bacterial strain belonging to the *Streptomyces* sp gender, deposited on Nov. 25, 2011 in the Agricultural Research Service Culture Collection (NRRL) of the U.S. Department of Agriculture with access number NRRL B-50602;

(iii) a bacterial strain belonging to the *Cellulosimicrobium* sp gender, deposited on Nov. 25, 2011 in the Agricultural Research Service Culture Collection (NRRL) of the U.S. Department of Agriculture with access number NRRL B-50603; and (iv) a bacterial strain belonging to the *Streptomyces* sp gender, deposited on Nov. 25, 2011 in the Agricultural Research Service Culture Collection (NRRL) of the U.S. Department of Agriculture with access number NRRL B-50601; and c) incubating the mixture.

2. The method as claimed in claim 1 wherein the soybean meal that is part of the substrate has a particles size between 200 and 600 μm.

3. The method as claimed in claim 2 wherein the soybean meal that is part of the substrate has a particle size of 400 μm.

4. The method as claimed in claim 3, wherein in step a) the soybean meal is mixed with water and then with a fermentation solution, wherein the fermentation solution comprises a pH buffer compound and a sulphate and/or a chloride of magnesium, calcium, nitrate, potassium, iron, manganese and zinc.

5. The method as claimed in claim 4, wherein the proportion of water/soybean meal is between 2:1 and 3:1 (v/w).

6. The method as claimed in claim 5 wherein the proportion of water/soybean meal is 2.4:1 (v/w).

7. The method as claimed in claim 4 wherein the fermentation solution comprises $MgSO_4$, CaCl, $NH_4CL$, KCl, FeSO pentahydrate, MnCl, $ZnSO_4$ pentahydrate, $H_3PO_4$ and $Na_2HPO_4$.

8. The method as claimed in claim 1, further comprising in step b) inoculating the soybean fermentation substrate with the selected bacterial strains and a mixture of water, soybean meal and fermentation solution.

9. The method as claimed in claim 8 wherein $10^7$ and $10^{11}$ cells of each selected strain per gram of substrate are inoculated.

10. The method as claimed in claim 9, wherein $10^9$ cells of each selected strain per gram of substrate are inoculated.

11. The method as claimed in claim 1, wherein in step c) of incubation the mixture of water, soybean meal, fermentation solution and bacteria is incubated at 37° C. during 6 to 14 days with rotation movements and the pH is kept between 6.5 and 7.5.

12. The method as claimed in claim 11, wherein the mixture is incubated for 10 days.

13. The method according to claim 1, further comprising step d) drying of the product.

14. A fermented soybean meal with reduced contents of non-starch polysaccharides and alpha-galactoside prepared by the method of claim 1, comprising an increase of protein between 12 and 15% with regards to the non fermented soybean meal with a degradation higher than 90% of the alpha-galactosides with respect to the non fermented soybean meal, with a reduction between 15 and 25% of non-starch polysaccharides (NSPs) and has an amino acid profile similar to that of the non fermented soybean meal.

15. The fermented soybean meal as claimed in claim 14 wherein the bacteria added in the bioprocess provides components that stay in the soybean meal and has immunostimulant effects when consumed.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer para 16S

```
<400> SEQUENCE: 1
cctacgggag gcagcag                                                    17

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer para 16S

<400> SEQUENCE: 2
ccgtcaattc mtttgagttt                                                 20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer para 16S

<400> SEQUENCE: 3
agaggtttga tcctggctca g                                               21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer para 16S

<400> SEQUENCE: 4
ggttaccttg ttacgactt                                                  19

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      primer para ITS

<400> SEQUENCE: 5
gaagtcgtaa caagg                                                      15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      primer para ITS

<400> SEQUENCE: 6
caaggcatcc accgt                                                      15
```